(12) United States Patent
Lin

(10) Patent No.: US 6,635,086 B2
(45) Date of Patent: Oct. 21, 2003

(54) IMPLANT FOR PLACEMENT BETWEEN CERVICAL VERTEBRAE

(75) Inventor: Paul S. Lin, Lewisburg, PA (US)

(73) Assignee: Blacksheep Technologies Incorporated, Lewisburg, PA (US)

( * ) Notice: Subject to any disclaimer, the term of this patent is extended or adjusted under 35 U.S.C. 154(b) by 23 days.

(21) Appl. No.: 09/870,284

(22) Filed: May 30, 2001

(65) Prior Publication Data
US 2002/0026243 A1 Feb. 28, 2002

Related U.S. Application Data
(60) Provisional application No. 60/207,930, filed on May 30, 2000.

(51) Int. Cl.$^7$ .................................................. A61F 2/44
(52) U.S. Cl. ..................................................... 623/17.11
(58) Field of Search ............................ 623/17.11–17.16

(56) References Cited

U.S. PATENT DOCUMENTS

| | | |
|---|---|---|
| 3,298,372 A | 1/1967 | Feinberg |
| 3,905,047 A | 9/1975 | Long |
| 3,916,907 A | 11/1975 | Peterson |
| 4,289,123 A | 9/1981 | Dunn |
| 4,349,921 A | 9/1982 | Kuntz |
| 4,401,112 A | 8/1983 | Rezaian |
| RE31,628 E | 7/1984 | Allgower et al. |
| 4,484,570 A | 11/1984 | Sutter et al. |
| 4,493,317 A | 1/1985 | Klaue |
| 4,611,581 A | 9/1986 | Steffee |
| 4,636,217 A | 1/1987 | Ogilvie et al. |
| 4,653,481 A | 3/1987 | Howland et al. |
| 4,655,199 A | 4/1987 | Steffee |
| 4,696,290 A | 9/1987 | Steffee |
| 4,714,469 A | 12/1987 | Kenna |
| 4,772,287 A | 9/1988 | Ray et al. |
| 4,790,297 A | 12/1988 | Luque |
| 4,820,305 A | 4/1989 | Harms et al. |
| 4,834,757 A | 5/1989 | Brantigan |
| 4,854,311 A | 8/1989 | Steffee |
| 4,878,915 A | 11/1989 | Brantigan |
| 4,898,161 A | 2/1990 | Grundei |
| 4,913,134 A | 4/1990 | Luque |
| 4,936,848 A | 6/1990 | Bagby |
| 4,961,740 A | 10/1990 | Ray et al. |
| 5,015,247 A | 5/1991 | Michelson |
| 5,015,255 A | 5/1991 | Kuslich |
| 5,026,373 A | 6/1991 | Ray et al. |
| 5,055,104 A | 10/1991 | Ray |
| 5,059,193 A | 10/1991 | Kuslich |
| 5,147,361 A | 9/1992 | Ojima et al. |
| 5,147,402 A | 9/1992 | Bohler et al. |
| 5,192,327 A | 3/1993 | Brantigan |

FOREIGN PATENT DOCUMENTS

| | | | |
|---|---|---|---|
| EP | WO 01/28463 A1 * | 4/2001 | ............... 623/17.11 |
| EP | WO 02/13731 A1 * | 2/2002 | ............... 623/17.11 |

OTHER PUBLICATIONS

Depraetere et al., Interbody Cages in PLIF Surgery, A Multicentric Report.
Brantigan, I/F Cage for PLIF, Acromed.
BAK?Proximity Posterior Interbody Fusion System, Spinetech.
Ray et al., A Prosterior Lmumbar Nucleus "Artificial Disc," Stryker Implants.
A Cellular Structural Biomaterial, Hedrocel.

*Primary Examiner*—David H. Willse
*Assistant Examiner*—Suzette J. Jackson
(74) *Attorney, Agent, or Firm*—Calfee, Halter & Griswold, LLP

(57) ABSTRACT

A stirrup shaped cervical implant is provided for use in keeping spinal vertebrae separated. The implant includes a ring portion connected to a truncation. The ring portion includes legs having barbed saw teeth. The crests of each of the barbed saw teeth are aligned to match the contours of the adjacent vertebra.

10 Claims, 4 Drawing Sheets

U.S. PATENT DOCUMENTS

| | | |
|---|---|---|
| 5,306,307 A | 4/1994 | Senter et al. |
| 5,334,194 A | 8/1994 | Mikhail |
| 5,364,399 A | 11/1994 | Lowery et al. |
| 5,380,324 A | 1/1995 | Müller et al. |
| 5,423,817 A | 6/1995 | Lin |
| 5,425,772 A | 6/1995 | Brantigan |
| 5,489,307 A | 2/1996 | Kuslich et al. |
| 5,489,308 A | 2/1996 | Kuslich et al. |
| 5,505,732 A | 4/1996 | Michelson |
| 5,514,180 A | 5/1996 | Heggeness et al. |
| 5,562,662 A | 10/1996 | Brumfield et al. |
| 5,607,424 A | 3/1997 | Tropiano |
| 5,609,635 A | 3/1997 | Michelson |
| 5,630,816 A | 5/1997 | Kambin |
| 5,653,761 A | 8/1997 | Pisharodi |
| 5,653,762 A | 8/1997 | Pisharodi |
| 5,658,336 A | 8/1997 | Pisharodi |
| 5,665,122 A | 9/1997 | Kambin |
| 5,676,666 A | 10/1997 | Oxland et al. |
| 5,683,391 A | 11/1997 | Boyd |
| 5,693,100 A | 12/1997 | Pisharodi |
| 5,709,683 A | 1/1998 | Bagby |
| 5,713,900 A | 2/1998 | Benzel et al. |
| 5,716,355 A | 2/1998 | Jackson et al. |
| 5,720,748 A | 2/1998 | Kuslich et al. |
| 5,766,252 A | 6/1998 | Henry et al. |
| 5,776,199 A | 7/1998 | Michelson |
| 5,785,710 A | 7/1998 | Michelson |
| 5,797,917 A | 8/1998 | Boyd et al. |
| 5,803,904 A | 9/1998 | Mehdizadeh |
| 5,860,977 A | 1/1999 | Zucherman et al. |
| 5,865,845 A | 2/1999 | Thalgott |
| 5,865,847 A | 2/1999 | Kohrs et al. |
| 5,888,227 A | 3/1999 | Cottle |
| 5,904,683 A | 5/1999 | Pohndorf et al. |
| 5,916,267 A | 6/1999 | Tienboon |
| 6,143,033 A * | 11/2000 | Paul et al. ............... 623/17.11 |
| 6,206,923 B1 | 3/2001 | Boyd et al. |
| 6,231,610 B1 | 5/2001 | Geisler |
| 6,241,771 B1 * | 6/2001 | Gresser et al. ........... 623/17.16 |
| 6,245,108 B1 * | 6/2001 | Biscup .................... 623/17.11 |
| 6,258,125 B1 | 7/2001 | Paul et al. |
| 6,371,988 B1 * | 4/2002 | Pafford et al. ........... 623/17.11 |
| 6,432,140 B1 * | 8/2002 | Lin ......................... 623/17.16 |

* cited by examiner

IMPLANT FOR PLACEMENT BETWEEN CERVICAL VERTEBRAE

PRIORITY CLAIM

This application claims the benefit of U.S. provisional patent application No. 60/207,930 filed on May 30, 2000, the entirety of which is hereby incorporated by reference.

FIELD OF THE INVENTION

This invention generally relates to prostheses for the spine and more specifically to an implant to separate adjacent cervical vertebrae.

BACKGROUND OF THE INVENTION

The spine is the central support column for the human body. The cervical region of the spine is located in the area of the neck and is comprised of cervical vertebrae separated by disks. A diseased spine suffers from deterioration of a vertebra, disk or both. Disks and vertebrae may also be damaged by physical causes as well. Surgical repair consists of fusing adjacent vertebrae together by means of a bone graft. It is necessary to keep the adjacent vertebrae spaced at a certain distance at the time the bone graft is growing and fusing the adjacent vertebrae together. Traditionally, this has been done mechanically. Typically, the systems are comprised of plates and screws or rods and screws.

Intervertebral implants may be used to replace or augment the method of grafting. A problem with grafting is that grafts are not always successful. Resorption of the graft results in a collapse of the area between the vertebrae. A permanent support structure such as an implant will not allow collapse. A problem with prior art intervertebral implants is that most are designed for use in the lumber section of the spine and thus have contoured surfaces which match the contour of the lumbar vertebrae. The cervical vertebrae have contours different from those of the lumbar vertebrae.

Another problem with prior art implants currently being used in the cervical section of the spine is that some implants which are formed as cages do not have superior strength characteristics. An implant which is simple to manufacture and has superior strength is desired.

SUMMARY OF THE INVENTION

The present invention overcomes disadvantages in the prior art by providing an improved cervical implant for holding spinal vertebrae apart. The implant is stirrup shaped and includes a ring portion having two legs and an interconnecting section. The legs of the ring portion are connected to a truncation which has a thickness which exceeds the thickness of the ring portion. The legs of the ring portion also includes upper and lower surfaces provided with barbed saw teeth, each tooth defined by a proximal face having a rearward tapered angle and a substantially vertical distal face and a rounded valley between each pair of adjacent teeth.

The invention, in the aspects described above, provides the advantage of a physical support device which prevents the collapse of adjacent vertebrae in the event a bone graft is unsuccessful. This device is easy to insert and has superior strength. These and other features, aspects and advantages of the present invention will be fully described by the following description, appended claims, and accompanying drawings.

DETAILED DESCRIPTION OF THE INVENTION

Figure 1:
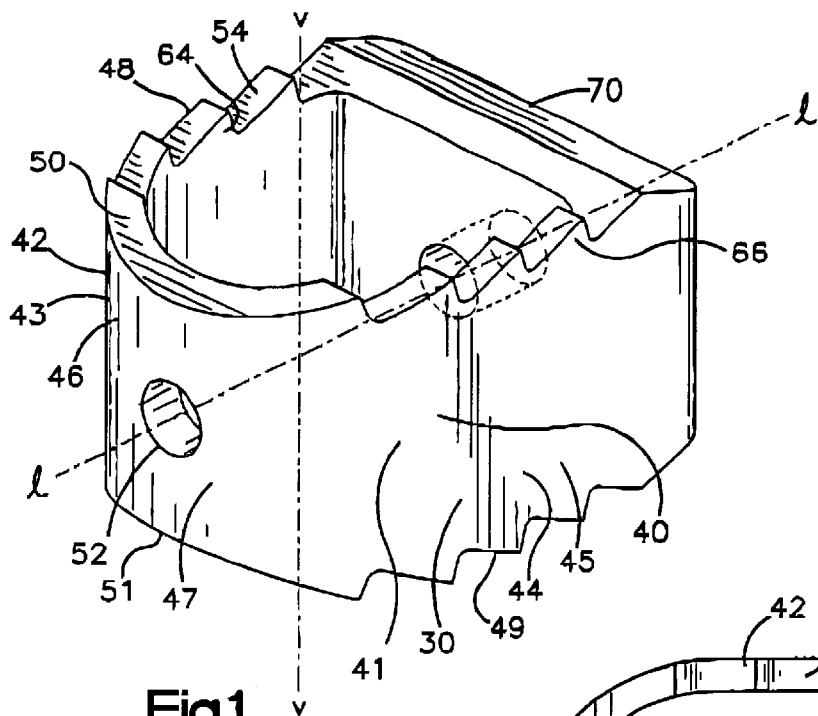
FIG. 1 is a perspective view of a cervical implant.
Figure 10:
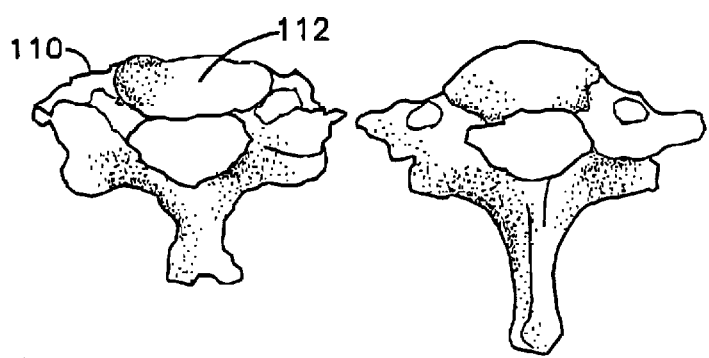
FIG. 10 is a top view of a pair of vertebrae.
Figure 11:
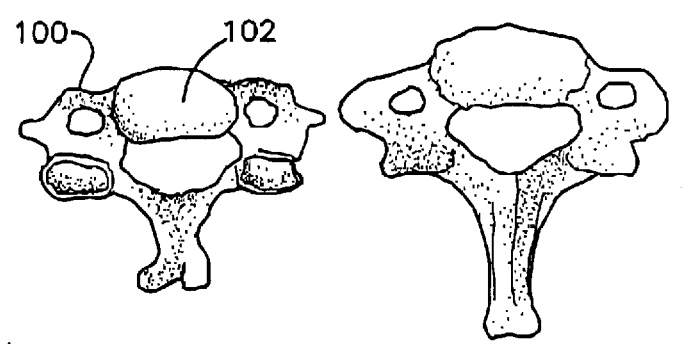
FIG. 11 is a bottom view of a pair of vertebrae.
Figure 12:
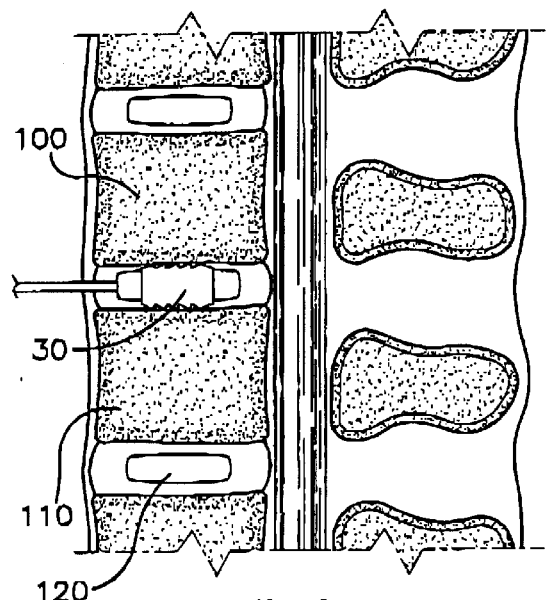
FIG. 12 is a cross-sectional side view of the spine with an implant being implanted in an anterior direction.
Figure 13:
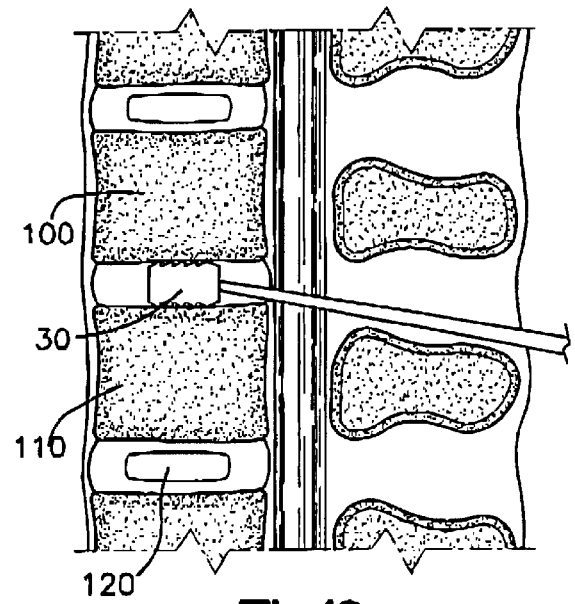
FIG. 13 is a cross-sectional side view of the spine with an implant being implanted in a posterior direction.

As shown in FIGS. 12 and 13, an intervertebral implant 30 may be inserted between two adjacent vertebrae 100 and 110. This procedure is most commonly done when the disc 120 between adjacent vertebrae is damaged or has been removed. FIG. 1 shows an intervertebral cervical implant 30 shaped to match the shape of the contact surface 102 of the upper cervical vertebra 100 and the contact surface 112 of the lower cervical vertebra 110 shown in FIGS. 10 and 11 which are adjacent to the implant 30 when it is placed within a human patient.

Referring back to FIG. 1, the implant 30 is stirrup shaped, having a ring portion 40 connected to a truncation 70 to form a solid having an open top and bottom. The ring portion 40 includes two legs 42 and 44 and an interconnecting section 46 between the two legs 42 and 44. Each leg 42 may be curved towards the interconnecting section 46 at the end connected to the interconnecting section 46. The exterior surfaces 43 and 45 of the legs 42 and 44 and exterior surface 47 of the interconnecting section 46 form the exterior surface 41 of the ring section 40 and this surface 41 is smooth. The legs 42 and 44 and the interconnecting section 46 have thicknesses which are equal. Each end of a leg 42 not connected to the interconnecting section 46 extends along a longitudinal axis "l" towards the truncation 70 and is connected to the truncation 70. Each leg 42 has an upper surface 48 and a lower surface 49.

Figure 2:
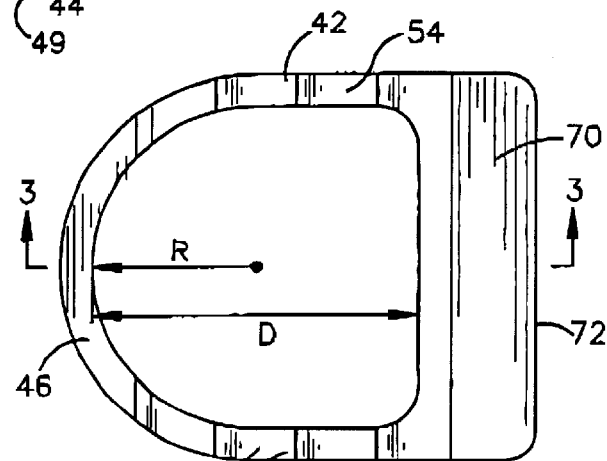
FIG. 2 is a top view of a cervical implant.
Figure 4:
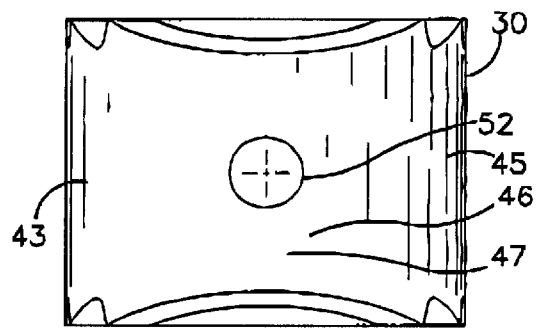
FIG. 4 is an end view of a cervical implant having arched saw tooth crests taken along the line 4—4 of FIG. 3.
Figure 5:
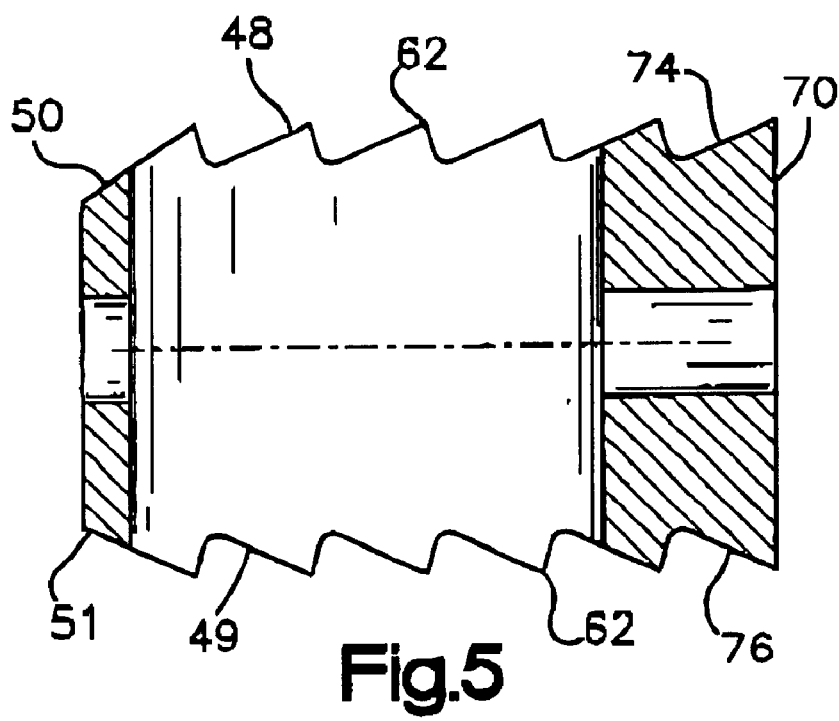
FIG. 5 is a cross-sectional view of an alternate embodiment of a cervical implant without a beveled truncation.

The interconnecting section 46 lies between each leg 42 and 44 of the ring portion 40. The interconnecting section 46 is curved, having a radius of curvature of approximately less than 3/16 of an inch. As shown in FIG. 2, in one embodiment of the invention, the radius of curvature R of the interconnecting section 46 does not exceed one half of the maximum distance D between the truncation 70 and the interconnecting section 46. The interconnecting section 46 includes upper and lower surfaces 50 and 51 which are beveled as shown in FIG. 5. The interconnecting section 46 also includes a convex exterior surface 47. The beveled surfaces 50 and 51 and convex exterior surface 47 ease insertion of the implant 30 between vertebrae. As shown in FIGS. 1 and 4, the interconnecting section 46 includes an aperture 52 which may be used for the attachment of tools used to insert, remove or align the implant 30 within a human body. The interior surface of the aperture 52 may be threaded to allow a secure fit to a threaded guiding device.

Figure 3:
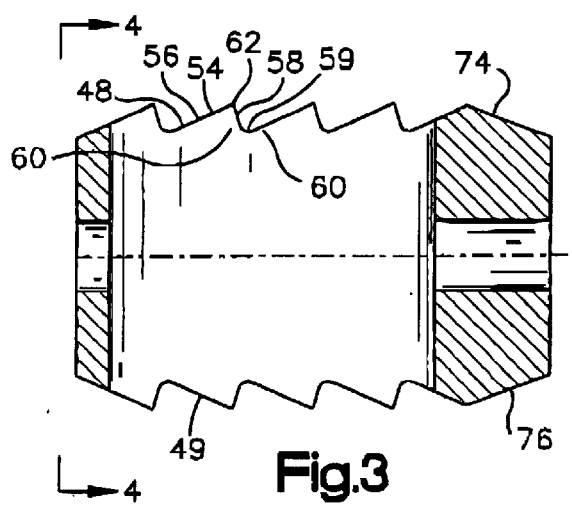
FIG. 3 is a cross-sectional view of a cervical implant taken along the line 3—3 of FIG. 2.

As shown in FIGS. 1–3, the implant 30 includes multiple biased metallic, angled barbs, also referred to as barbed saw teeth, or vertebral engagement points 54. The barbed saw teeth 54 are positioned along and rise above the upper surfaces 48 of the legs and the lower surfaces 49 of the legs. The barbed saw teeth 54 are defined by proximal faces 56 and distal faces 58. The proximal face 56 of a barbed saw tooth 54 may be angled rearwardly relative to the direction of insertion of the implant 30. The distal face 58 may be angled in a substantially vertical manner. The distal face 58 may also be angled rearwardly relative to the direction of insertion of the implant 30. A rounded valley 59 is between the bases 60 of each barbed saw tooth 54. The overall rearward angular orientation of the barbed saw teeth 54 allows the implant 30 to be inserted without significant resistance as shown in FIG. 12. Once inserted, the angular orientation resists retropulsion and implant migration.

Figure 6:
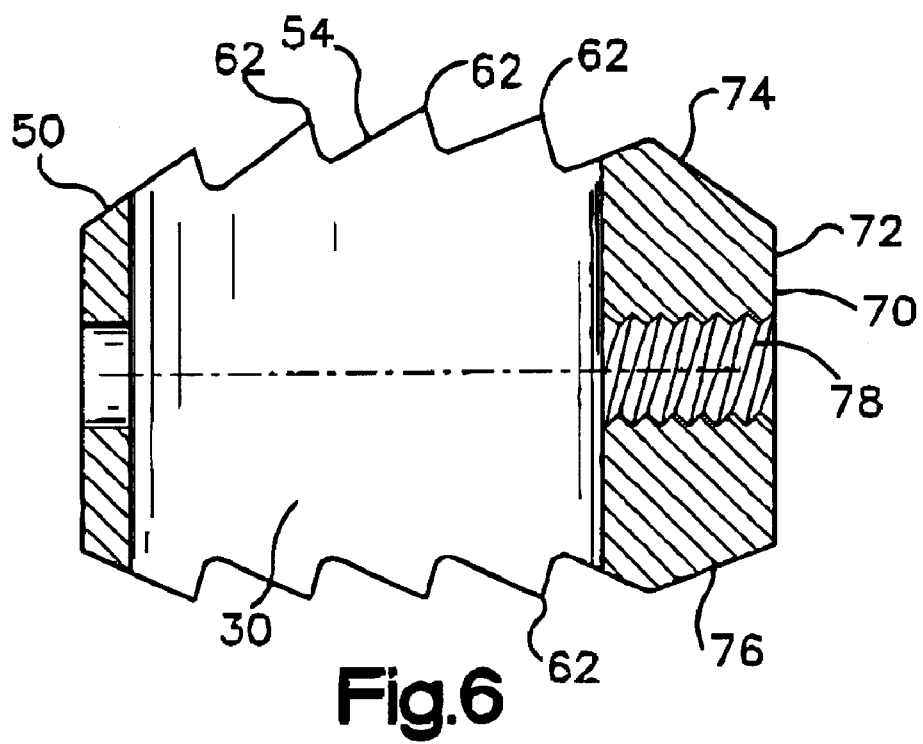
FIG. 6 is a cross-sectional view of an alternate embodiment of a cervical implant having arched saw tooth crests.

As shown in FIGS. 3 and 12, each barbed saw tooth 54 includes a crest 62 at the point of the tooth. The crests 62 of the barbed saw teeth 54 are sharp to permit easy entry into bone of the upper adjacent vertebra 100 and the lower adjacent vertebra 110. The orientation of the crests 62 of adjacent barbed saw teeth 54 varies depending upon the shape of the upper and lower cervical vertebra 100 and 110 between which the implant 30 is placed. For example, as shown in FIG. 6, the crests 62 of the barbed saw teeth 54 are arched. Because of the arch shape, the crest height of one saw tooth varies from the crest height on the adjacent saw tooth.

FIG. 5 shows an implant 30 used when the arc of the upper adjacent vertebra 100 is very slight or nil, while FIG. 6 shows the embodiment which is used when the arc of the upper adjacent vertebra 100 is large. The crests 62 rising from the lower surfaces 49 of the legs 40 and 42 are not arched because there is no arc to the contact surface 112 of the lower adjacent vertebra 110. However, if the lower adjacent vertebra 110 has an arc, the crests rising from the lower surface 49 of the legs may be arched to correspond to the vertebral contact surface 112. Identification marks may be printed on the exterior surface 43 of one or both legs 42 and 44, but are not necessary.

Although each leg surface may include any number of barbed saw teeth 54, in an embodiment of the invention, the number of barbed saw teeth 54 upon any upper or lower surface 48 and 49 of an individual leg does not exceed six. As shown in FIG. 1, each barbed saw tooth 54 includes an interior 64 and an exterior side 66. The exterior side 66 of each barbed saw tooth 54 is planer (lying in the same plane) as the exterior surface of the legs 43 and 45 or interconnecting section 47. The interior side 64 of each barbed saw tooth 54 is likewise planer with the interior surface of the legs or interconnecting section.

As shown in FIG. 2, the truncation 70 has an exterior surface 72 which may be flat. As shown in FIG. 5, the truncation 70 may have an upper surface 74 and a lower surface 76 which matches the shape of a barbed saw tooth 54 upon an adjacent leg. Alternatively, as shown in FIG. 6, the upper surface 74 of the truncation 70 may be partially beveled into the exterior surface 72 of the truncation 70. A beveled corner may also exist between the lower surface 76 of the truncation 70 and the exterior surface 72 of the truncation 70. A threaded or non-threaded aperture 78 may be centered within the truncation 70 and allows the implant 30 to be placed, adjusted, and removed using a positioning tool. The beveled edge 50 of the interconnecting portion 46 and the truncation 70 also act to engage the verterbral surface. The thickness of the truncation 70 exceeds the thickness of any part of the ring section 40 (legs or interconnecting section).

Figure 14:
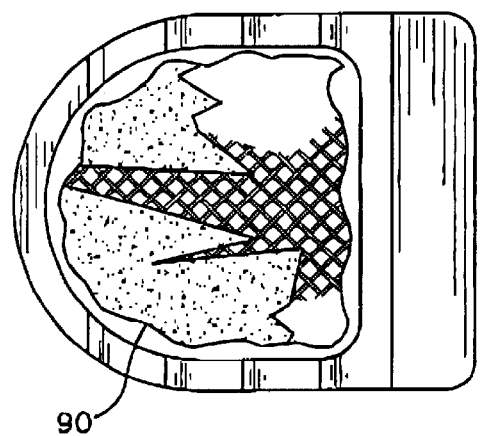
FIG. 14 is a top view of a cervical implant packed with bone graft material.

The implant 30 may be manufactured from titanium, but may be manufactured from other materials compatible with the human body such as stainless steel or ceramic materials. As shown in FIG. 14, within the ring section 40, bone graft material may be placed. The material may be inside of a porous bag 90. Bone graft material aids in fusing the upper adjacent vertebra 100 to the lower adjacent vertebra 110.

Figure 7:
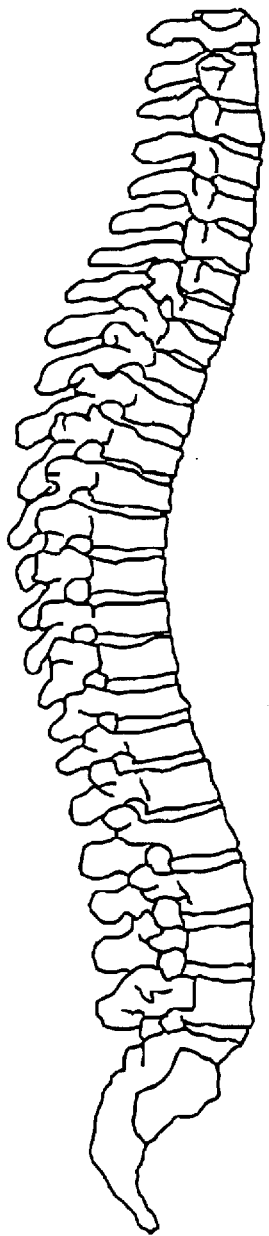
FIG. 7 is a schematic illustration of the human spine with one of the cervical vertebrae highlighted.
Figure 8:
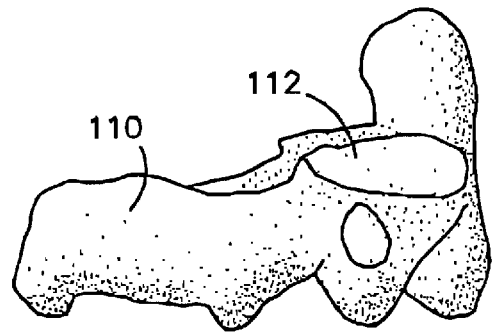
FIGS. 8 & 9 are lateral views of a single vertebra.
Figure 9:
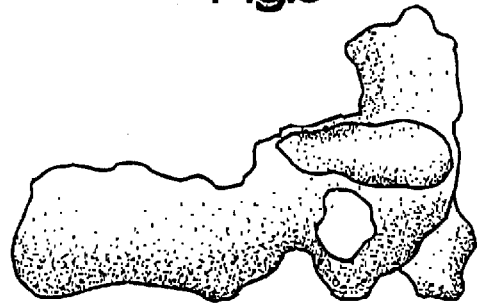

The implant 30 may be inserted anteriorly into the cervical area of the spine as shown in FIG. 12. The implant 30 is oriented between the vertebrae 100 and 110 with the longitudinal axis "l", seen in FIG. 1, of the implant 30 aligned with the plane of the vertebral faces. The vertical axis "v" of the implant 30 is aligned with the length of the entire human spine (example shown in FIG. 7). Thus, the open top and bottom of the cervical implant 30 abut the contact surfaces 102 and 112 of the vertebrae and the barbed saw teeth 54 bite into these surfaces. The beveled surfaces of the interconnecting portion 46 and the truncation 70 also act to engage the vertebral contact surfaces. Before insertion of an implant 30, preferably a discectomy is performed to first remove the diseased or damaged parts of the spinal disc 120. If necessary the adjacent vertebrae 100 and 110 may be spread using tools known to those skilled in the art. Alternatively, no spreading is required if the vertebrae have not collapsed into an undesired position. The implant 30 may also be inserted posteriorly as shown in FIG. 13.

A single implant 30 may be used between a pair of adjacent vertebrae 100 and 110, but it is also possible to use more than one implant 30 if the contact area 102 on the upper vertebra and the contact area 112 on the lower vertebra are large. Although the invention has been shown and described with reference to certain preferred and alternate embodiments, the invention is not limited to these specific embodiments. Minor variations and insubstantial differences in the various combinations of materials and methods of application may occur to those of ordinary skill in the art while remaining within the scope of the invention as claimed and equivalents.

What is claimed is:

1. A stirrup shaped intervertebral implant for placement between upper and lower cervical vertebrae comprising:
    a ring portion including two legs and an interconnecting section, said legs and interconnecting section having a consistent and equal thickness;
    a truncation interconnecting said legs of said ring portion, said truncation having a thickness exceeding said thickness of the ring portion;
    said ring portion legs having upper surfaces and lower surfaces, each upper and lower surface provides with a plurality of barbed saw teeth; and
    each of said barbed saw teeth defined by proximal faces having rearward tapered angles, substantially vertical distal faces, and rounded valleys between adjacent barbed saw teeth.

2. The intervertebral implant of claim 1 wherein said truncation further includes an aperture for attachment of an insertion tool.

3. The intervertebral implant of claim 2 wherein said interconnecting section further includes an aperture for attachment of an insertion tool.

4. The intervertebral implant of claim 1 wherein a bag of bone graft material is located within the interior of the ring portion.

5. The intervertebral implant of claim 1 wherein said barbed saw teeth have planer sides.

6. The intervertebral implant of claim 1 wherein said ring portion and truncation have smooth exterior surfaces.

7. A stirrup shaped intervertebral implant for placement between upper and lower cervical vertebrae comprising:

a ring portion including two legs and an interconnecting section, said legs and interconnecting section having equal thickness;

a truncation interconnecting said legs of said ring portion, said truncation having a thickness exceeding said thickness of the ring portion;

said ring portion legs having upper surfaces and lower surfaces, each upper and lower surface provided with a plurality of barbed saw teeth; and each of said barbed saw teeth defined by proximal faces having rearward tapered angles, substantially vertical distal faces, and rounded valleys between adjacent barbed saw teeth and wherein said barbed saw teeth on said upper surface of said ring portion legs are further defined by upper crests raised to a height above said upper surface of said ring portion leg, the height of said upper crest varying from the height of said upper crest on an adjacent barbed saw tooth;

said upper crest heights arranged in an arc which substantially matches the contour of the upper vertebra to which the barbed saw teeth engage; and said barbed saw teeth of said lower surface of said ring portion legs further defined by crests having an equal height above said lower surface of said ring portion leg.

8. A stirrup shaped intervertebral implant for placement between upper and lower cervical vertebrae comprising:

a ring portion including two legs and an interconnecting section, said legs and interconnecting section having equal thickness;

a truncation interconnecting said legs of said ring portion, said truncation having a thickness exceeding said thickness of the ring portion;

said ring portion legs having upper surfaces and lower surfaces, each upper and lower surface provided with a plurality of barbed saw teeth wherein the number of barbed saw teeth on each ring portion leg upper and lower surfaces does not exceed six; and each of said barbed saw teeth defined by proximal faces having rearward tapered angles, substantially vertical distal faces, and rounded valleys between adjacent barbed saw teeth.

9. A stirrup shaped intervertebral implant for placement between upper and lower cervical vertebrae comprising:

a ring portion including two legs and an interconnecting section, said legs and interconnecting section having equal thickness;

a truncation interconnecting said legs of said ring portion, said truncation having a thickness exceeding said thickness of the ring portion wherein the radius of curvature of the interconnecting section does not exceed one half of the maximum distance between the truncation and the interconnecting section;

said ring portion legs having upper surfaces and lower surfaces, each upper and lower surface provided with a plurality of barbed saw teeth; and each of said barbed saw teeth defined by proximal faces having rearward tapered angles, substantially vertical distal faces, and rounded valleys between adjacent barbed saw teeth.

10. A stirrup shaped intervertebral implant for placement between upper and lower cervical vertebrae comprising:

a ring portion including two legs and an interconnecting section, said legs and interconnecting section having equal thickness;

a truncation interconnecting said legs of said ring portion, said truncation having a thickness exceeding said thickness of the ring portion wherein said truncation includes beveled upper and lower surfaces;

said ring portion legs having upper surfaces and lower surfaces, each upper and lower surface provided with a plurality of barbed saw teeth; and each of said barbed saw teeth defined by proximal faces having rearward tapered angles, substantially vertical distal faces, and rounded valleys between adjacent barbed saw teeth.

* * * * *

UNITED STATES PATENT AND TRADEMARK OFFICE
CERTIFICATE OF CORRECTION

PATENT NO. : 6,635,086 B2  Page 1 of 1
DATED : October 21, 2003
INVENTOR(S) : Paul S. Lin It is certified that error appears in the above-identified patent and that said Letters Patent is hereby corrected as shown below:

Column 4,
Line 51, please delete "provides" and insert -- provided --.

Signed and Sealed this

Thirtieth Day of December, 2003

JAMES E. ROGAN
*Director of the United States Patent and Trademark Office*